United States Patent [19]

Yamada et al.

[11] Patent Number: 5,434,148

[45] Date of Patent: Jul. 18, 1995

[54] β-CARBOLINE DERIVATIVE

[75] Inventors: Koichiro Yamada, Saitama; Masataka Hikota, Shiki; Takeshi Yura, Takarazuka; Toshiro Shikano, Omiya; Masaaki Nagasaki, Urawa, all of Japan

[73] Assignee: Tanabe Seiyaku Co., Ltd., Osaka, Japan

[21] Appl. No.: 67,931

[22] Filed: May 27, 1993

[30] Foreign Application Priority Data

May 28, 1992 [JP] Japan ................. 4-136819

[51] Int. Cl.⁶ ............. C07D 471/04; C07D 487/04; A61K 31/55; A61K 31/44
[52] U.S. Cl. .................. 514/213; 514/292; 540/524; 546/87
[58] Field of Search .............. 546/87; 514/292, 213; 540/524

[56] References Cited

U.S. PATENT DOCUMENTS

| | | | |
|---|---|---|---|
| 4,001,263 | 1/1977 | Plattner et al. | 546/86 |
| 4,981,847 | 1/1991 | Sato et al. | 514/211 |
| 4,992,437 | 2/1991 | Naka et al. | 514/220 |

FOREIGN PATENT DOCUMENTS

| | | | |
|---|---|---|---|
| 0304223 | 2/1989 | European Pat. Off. | 546/87 |
| 0304223A2 | 2/1989 | European Pat. Off. | 546/87 |
| 0434360A1 | 6/1991 | European Pat. Off. | 514/292 |
| 0487207A1 | 5/1992 | European Pat. Off. | 540/485 |
| 9200295 | 1/1992 | WIPO | 546/87 |
| 9204348 | 3/1992 | WIPO | 546/87 |

OTHER PUBLICATIONS

Lippke et al. (1985) *Journal of Pharmaceutical Sciences* 74(6):676-80.
Ganong, William F., MD, "Regulation of Gastrointestinal Function," *Review of Medical Physiology*, 15th Ed., pp. 451-452 (1991).
Kerwin, *Drugs of the Future*, vol. 16, No. 12, pp. 1111-1119 (1991).

*Primary Examiner*—Alan L. Rotman
*Attorney, Agent, or Firm*—Birch, Stewart, Kolasch & Birch

[57] ABSTRACT

Disclosed are β-carboline derivatives represented by the formula:

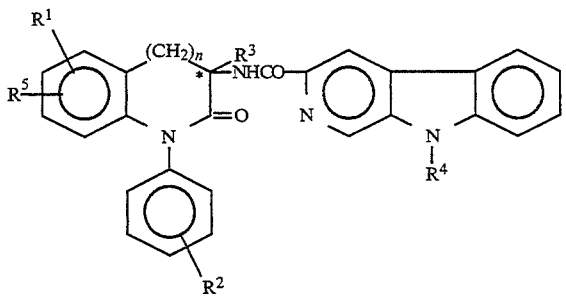

wherein $R^1$ represents hydrogen atom, a lower alkyl group, a lower alkoxy group or hydroxy group; $R^5$ represents hydrogen atom, or $R^1$ and $R^5$ are bonded to represent a lower alkylenedioxy group; $R^2$ represents hydrogen atom, a halogen atom, a lower alkoxy group or hydroxy group; $R^3$ represents hydrogen atom, a carbamoyl lower alkyl group, a lower alkyl group, a carboxy lower alkyl group or a lower alkoxycarbonyl lower alkyl group; $R^4$ represents hydrogen atom, a lower alkyl group, a carboxy lower alkyl group, a lower alkoxycarbonyl lower alkyl group, a lower alkanoyl group, an arylcarbonyl group, a lower alkanesulfonyl group, a lower alkoxycarbonyl group, an aralkyl group, formyl group or a di(lower alkyl)sulfamoyl group; n represents 0, 1 or 2; and the symbol * represents an asymmetric carbon atom, or a pharmaceutically acceptable salt thereof, and a process for preparing the same.

14 Claims, No Drawings

β-CARBOLINE DERIVATIVE

BACKGROUND OF THE INVENTION

This invention relates to novel β-carboline derivatives having an excellent antagonistic acton on cholecystokinin receptors and which are useful for preventing and curing pancreatic disorder and gastrointestinal diseases, and also relates to a process for preparing the same.

Cholecystokinin (CCK) is a brain-gutpeptide existing in the gastrointestinal tract and central nervous system. It has been known as a substance which is concerned with control of pancreatic exocrine secretion and control of appetite, and has been considered to promote the motility of the colon, contract the gallbladder, secrete pancreatic enzymes and inhibit emptying of gastric contents. Further, cholecystokinin coexists with dopamine in a central nervous system so that it has been also considered to have a role concerned with the mechanism of the dopaminergic system.

It has been considered that a substance having an antagonistic action on cholecystokinin receptor is effective for preventing or curing pancreatic disorder and gastrointestinal diseases so that a number of antagonists have been studied up to the present. For example, as a cholecystokinin antagonist, there have been known peptide type antagonistic substances such as benzotrypto. However, such substances are not necessarily satisfactory in that activities thereof are relatively weak, duration of action is short time, and these are unstable and poor in absorption.

As a non-peptide type antagonistic substance, there have been disclosed a benzodiazepine compound in Japanese Provisional Patent Publication No. 111774/1990 and a thienoazepine compound in Japanese Provisional Patent Publication No. 28181/1990. Further, in Japanese Provisional Patent Publication No. 68369/1989, there have been disclosed β-carboline derivatives including a compound of the formula (IV):

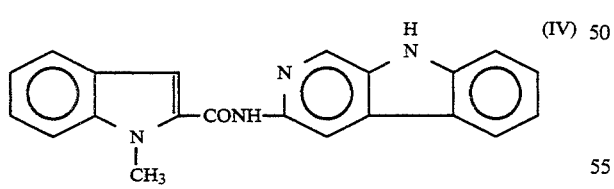

SUMMARY OF THE INVENTION

The present inventors have studied intensively in order to obtain a substance having an excellent antagonistic action on a cholecystokinin receptor, and which useful as a medicine, and have consequently found that a certain kind of a β-carboline derivative can achieve such an object, to accomplish the present invention.

Accordingly, the present invention is to provide a β-carboline derivative represented by the formula (I):

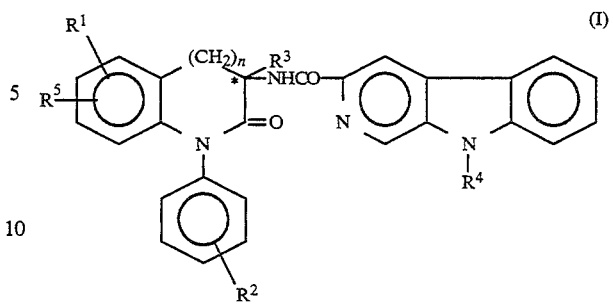

wherein $R^1$ represents hydrogen atom, a lower alkyl group, a lower alkoxy group or hydroxy group; $R^5$ represents hydrogen atom, or $R^1$ and $R^5$ are bonded to represent a lower alkylenedioxy group; $R^2$ represents hydrogen atom, a halogen atom, a lower alkoxy group or hydroxy group; $R^3$ represents hydrogen atom, a lower alkyl group, a carboxy lower alkyl group or a lower alkoxycarbonyl lower alkyl group; $R^4$ represents hydrogen atom, a lower alkyl group, a carboxy lower alkyl group, a lower alkoxycarbonyl lower alkyl group, a lower alkanoyl group, an arylcarbonyl group, a lower alkanesulfonyl group, a lower alkoxycarbonyl group, an aralkyl group, formyl group or a di(lower alkyl)sulfamoyl group; n represents 0, 1 or 2; and the symbol * represents an asymmetric carbon atom, and a pharmacologically acceptable salt thereof.

The present invention also provide a process for preparing the same which comprises reacting an amine compound represented by the formula (II):

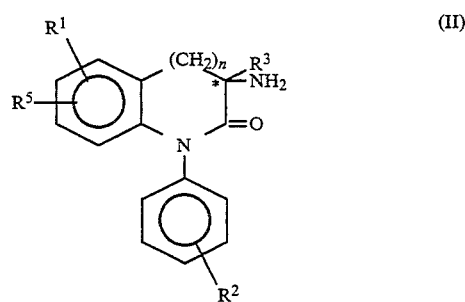

wherein $R^1$, $R^2$, $R^3$, $R^5$, n and * have the same meanings as defined above, or a salt thereof with a carboxylic acid compound represented by the formula (III):

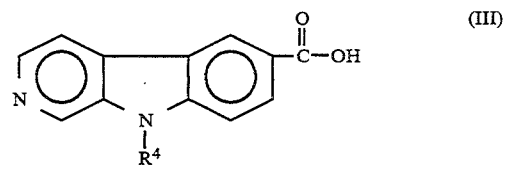

wherein $R^4$ has the same meaning as defined above, a reactive derivative thereof or a salt thereof.

DESCRIPTION OF THE PREFERRED EMBODIMENTS

The desired compound (I) is a medical compound having an excellent antagonistic action on a cholecystokinin receptor and is useful as a prophylactic or curing agent for pancreatic disorders and gastrointestinal diseases.

Among the desired compounds of the present invention, as a pharmaceutically preferred compound, there may be mentioned a compound of the formula (I) wherein $R^1$ is hydrogen atom, a lower alkyl group, a lower alkoxy group or hydroxy group, $R^2$ is hydrogen atom or a halogen atom, $R^3$ is hydrogen atom, a lower alkyl group, a carboxy lower alkyl group or a lower alkoxycarbonyl lower alkyl group, $R^4$ is hydrogen atom, a lower alkyl group, a formyl group, a lower alkoxycarbonyl lower alkyl group or a lower alkanoyl group, and $R^5$ is hydrogen atom.

As a more preferred compound in view of pharmaceutical effects, there may be mentioned a compound of the formula (I) wherein $R^1$ is hydrogen atom or a lower alkoxy group, $R^2$ is hydrogen atom or a halogen atom, $R^3$ is hydrogen atom, a lower alkyl group or a lower alkoxycarbonyl lower alkyl group, $R^4$ is hydrogen atom, a lower alkyl group or a lower alkanoyl group, and $R^5$ is hydrogen atom.

As a pharmaceutically most preferred compound, there may be mentioned a compound of the formula (I) wherein $R^1$ is hydrogen atom or methoxy group (preferably methoxy group), $R^2$ is hydrogen atom or fluorine atom (preferably fluorine atom), $R^3$ is hydrogen atom, methyl group or methoxycarbonylethyl group (preferably methyl group), $R^4$ is hydrogen atom or acetyl group (preferably acetyl group), and $R^5$ is hydrogen atom.

In the formula (I), optical isomers based on the asymmetric carbon atom * may exist. Both of these optical isomers and a mixture thereof are included in the desired compounds of the present invention°

The desired compound of the present invention can be used for medical uses in the free form or in the form of a pharmaceutically acceptable salt thereof. As such a salt, there may be mentioned an acid addition salt with an inorganic acid or an organic acid, and a salt with an inorganic base, an organic base or an amino acid, for example, hydrochloride, sulfate, hydrobromide, methanesulfonate, fumarate, maleate, an alkali metal (e.g. sodium and potassium) salt, a methylamine salt, a diethylamine salt, a triethylamine salt and a salt with lysine.

The desired compound (I) and pharmaceutically acceptable salts thereof can be administered orally and parenterally, and can be generally administered to mammals including a human being in the form of common medical compositions such as a capsule, a microcapsule, a tablet, a granule, a powder, a troche, a syrup, an aerosol, an inhalation, a solution, an injection, a suspension, an emulsion and a suppository.

The medical composition of the present invention may contain various organic or inorganic carrier substances commonly used for medicines, including an excipient such as sucrose, starch, mannitol, sorbitol, lactose, glucose, cellulose, talc, calcium phosphate and calcium carbonate; a binder such as cellulose, methyl cellulose, hydroxypropyl cellulose, polypropyl pyrrolidone, gelatin, gum arabic, polyethylene glycol, sucrose and starch; a disintegrating agent such as starch, carboxymethyl cellulose, a calcium salt of carboxymethyl cellulose, hydroxypropyl starch, sodium glycol starch, sodium hydrogen carbonate, calcium phosphate and calcium citrate; a lubricant such as magnesium stearate, talc and sodium lauryl sulfate; a fragrant such as citric acid, menthol, glycine and orange powder; a preservative such as sodium benzoate, sodium hydrogen sulfite, methylparaben and propylparaben; a stabilizer such as citric acid, sodium citrate and acetic acid; a suspending agent such as methyl cellulose, polyvinyl pyrrolidone and aluminum stearate; a dispersant; an aqueous diluting agent such as water; and a base wax such as cacao butter, polyethylene glycol and illuminating kerosine.

The dose of the desired compound (I) of the present invention or a pharmaceutically acceptable salt thereof varies depending on age, body weight and state of a patient or an administration method, but it is generally 0.01 mg/kg to 50 mg/kg per day.

According to the present invention, the desired β-carboline derivative (I) can be prepared as described above.

The reactive derivative of the compound (III) may include acid halides, reactive esters and acid anhydrides, preferably an acid halide such as acid chloride.

As the salts of the compounds (II) and (III), there may be used, for example, a salt with an inorganic acid such as hydrochloride and sulfate.

The reaction of the amine compound (II) or a salt thereof and the carboxylic acid compound (III), a reactive derivative thereof or a salt thereof can be carried out easily according to a conventional method. For example, the reaction of the amine compound (II) or a salt thereof and an reactive derivative or a salt of the carboxylic acid compound (III) is carried out in a solvent, if necessary, in the presence of an acid acceptor, at a temperature of under cooling to up to a boiling point of a solvent used.

The solvent to be used is not particularly limited so long as it is a solvent inactive to the reaction, and may include, for example, water; alcohols such as methanol, ethanol, propanol and butanol; ethers such as tetrahydrofuran, diethyl ether and dioxane; hydrocarbons such as petroleum ether, hexane and cyclohexane; halogenated hydrocarbons such as dichloromethane, dichloroethane and chloroform; aromatic hydrocarbons such as benzene, toluene and xylene; amides such as N,N-dimethylformamide and N,N-dimethylacetamide, and a mixed solvent of them.

As the acid acceptor to be optionally used, there may be mentioned organic bases such as triethylamine, pyridine, picoline and N-methylmorpholine; alkali metal hydroxides such as sodium hydroxide and potassium hydroxide; and alkali metal carbonates such as sodium carbonate, sodium hydrogen carbonate and potassium carbonate, preferably triethylamine and pyridine. As hydrated solvents, sodium hydrogen carbonate and potassium carbonate are preferred.

The reaction of the amine compound (II) or a salt thereof and the free carboxylic acid compound (III) or a salt thereof can be carried out in a solvent in the presence of a dehydrating agent.

The dehydrating agent is preferably a dehydrating agent used for amide synthesis, and may include, for example, dicyclohexyl carbodiimide, N-methyl-2-chloropyridinium iodide, 1-ethyl-3-(3'-dimethylaminopropyl)carbodiimide hydrochloride, a BOP reagent (benzotriazol-1-yloxytris(dimethylamino)phosphonium hexafluorophosphate) and diphenylphosphoryl azide (DPPA).

As the solvent, there may be preferably used those described above. The reaction proceeds preferably under cooling to under heating.

The present reaction proceeds without racemization so that an optically active desired compound can be obtained by using an optically active starting material.

Further, the desired compound (I) of the present invention can be also prepared by converting the desired compound obtained as described above into another desired compound according to a conventional method, Such a mutually converting reaction between the desired compounds may be selected suitably depending on the kind of a functional group possessed by the compounds, and may be carried out by, for example, the following methods.

Method (a):

The desired compound (I) in which $R^4$ is a lower alkanoyl group or a lower alkanesulfonyl group can be prepared by reacting a compound represented by the formula (V):

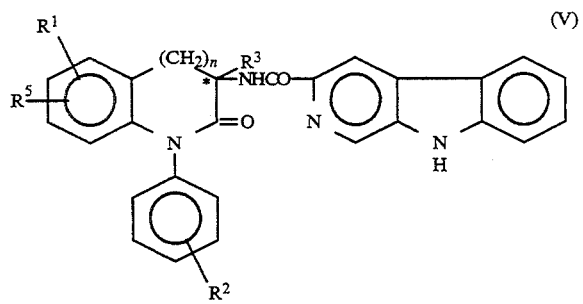

wherein $R^1$, $R^2$, $R^3$, $R^5$, n and * have the same meanings as defined above,
with a lower alkanoylating agent or a lower alkanesulfonylating agent, respectively.

As the lower alkanoylating agent, there may be mentioned acid anhydrides such as acetic anhydride, propionic anhydride, butyric anhydride and valeric anhydride; and acid halides such as acetyl chloride. As the lower alkanesulfonylating agent, there may be mentioned methanesulfonyl chloride. The reaction is carried out without a solvent or in a solvent in the presence of an acid acceptor. As the acid acceptor, there may be used those described in the above reaction of the amine compound (II) and the carboxylic acid compound (III).

Method (b):

The desired compound (I) in which $R^4$ is hydrogen atom can be prepared by deacylating a compound of the formula (I) wherein $R^4$ is a lower alkanoyl group.

The deacylating reaction can be carried out easily according to a conventional method, and it can be carried out by, for example, treating the compound (I) in which $R^4$ is a lower alkanoyl group in a solvent with an acid or an alkaline reagent. As the acid, there may be mentioned inorganic or organic acids such as mineral acids (e.g. hydrochloric acid, hydrobromic acid and sulfuric acid), trifluoroacetic acid, benzenesulfonic acid and p-toluene-sulfonic acid. As the alkaline reagent, there may be mentioned inorganic or organic bases such as alkali metal hydroxides (e.g. sodium hydroxide and potassium hydroxide), pyridine and ammonia.

Method (c):

The desired compound (I) in which at least one of $R^1$ and $R^2$ is hydroxy group can be prepared by dealkylating a compound represented by the formula (VI):

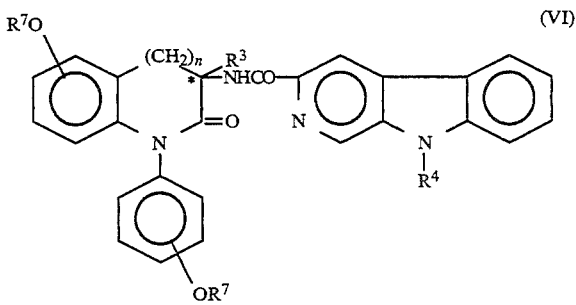

wherein $R^3$, $R^4$, n and * have the same meanings as defined above, and $R^7$ represents a lower alkyl group.

The dealkylating reaction can be carried out by reacting the compound (VI) with a hydrogen halide such as hydrogen chloride, hydrogen bromide and hydrogen iodide; a Lewis acid such as aluminum trichloride and boron tribromide; a mixture of aluminum trichloride and a thiol compound, or trimethylsilyl iodide, preferably boron tribromide.

Method (d):

The desired compound (I) in which at least one of $R^3$ and $R^4$ is a lower alkyl group, a carboxy lower alkyl group or a lower alkoxycarbonyl lower alkyl group can be prepared by reacting a compound of the formula (I) wherein at least one of $R^3$ and $R^4$ is hydrogen atom with an alkylating agent corresponding to at least one of $R^3$ and $R^4$ (that is, a lower alkylating agent, a carboxy lower alkylating agent or a lower alkoxycarbonyl lower alkylating agent). As these alkylating agents, there may be used corresponding alkyl halides (e.g. methyl iodide and ethyl bromoacetate), alkenes (e.g. methyl acrylate). The reaction can be carried out in a solvent in the presence of a base. As the base, there may be mentioned alkali metal carbonates such as potassium carbonate, sodium carbonate, sodium hydrogen carbonate and potassium hydrogen carbonate, organic bases such as 1,8-diazabicyclo[5.4.0]undec-7-ene, and alkali metal hydroxides such as sodium hydroxide and potassium hydroxide. The reaction can be carried out under inactive gaseous atmosphere such as argon, if necessary.

Method (e):

The desired compound (I) in which at least one of $R^3$ and $R^4$ is a carboxy lower alkyl group can be prepared by hydrolyzing a compound of the formula (I) wherein at least one of $R^3$ and $R^4$ is a lower alkoxycarbonyl lower alkyl group. The hydrolysis can be carried out in the same manner as in the deacylating reaction described in Method (b).

Method (f):

The desired compound (I) in which at least one of $R^3$ and $R^4$ is a lower alkoxycarbonyl lower alkyl group can be prepared by esterifying a compound of the formula (I) wherein at least one of $R^3$ and $R^4$ is a carboxy lower alkyl group. The esterification can be carried out easily by reacting with an alcohol in the presence of hydrogen chloride or an acid such as sulfuric acid.

All reactions in the above (a) to (f) are carried out at a temperature of under cooling to up to a boiling point of a solvent used.

The solvent to be used is not particularly limited so long as it is a solvent inactive to these reactions, and may include, for example, water, acetone, acetonitrile, hexane, cyclohexane, benzene, toluene, chloroform, dichloromethane, dichloroethane, tetrahydrofuran, N,N-dimethylformamide, N,N-dimethylacetamide or a mixture of them, which may be suitably selected depending on the kind of the reaction.

The respective reactions in the above (a) to (f) except for (d) proceed without racemization so that an optically active desired compound can be obtained by using an optically active substance as a starting material.

The β-carboline derivatives obtained by the above preparation processes can be isolated from the reaction mixtures according to a conventional method after completion of the reactions, and can be purified according to a conventional method, if desired. For example, after an excessive reagent is decomposed or a reaction solvent is removed after completion of the reaction, if necessary, the desired compound is can be collected by extraction with a soluble solvent or precipitation by adding an insoluble solvent. Further, the desired compound can be purified by column chromatography or recrystallization, if necessary.

The amino compound represented by the formula (II), which is a starting material, can be prepared according to Schemes 1 to 5 shown below.

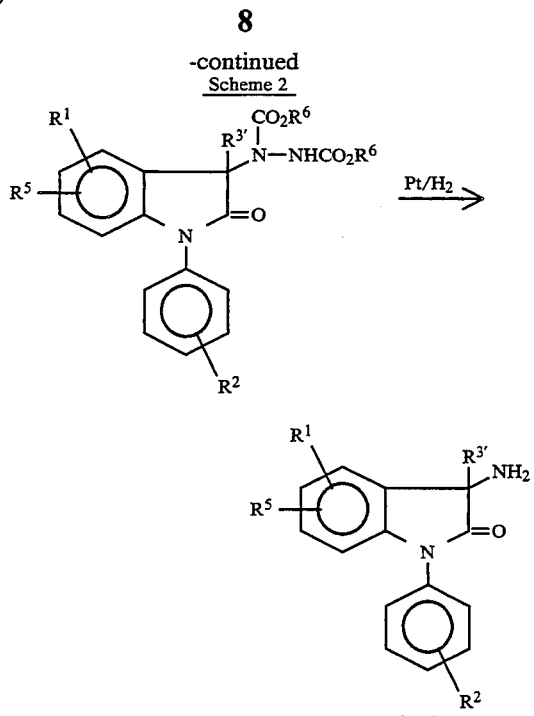

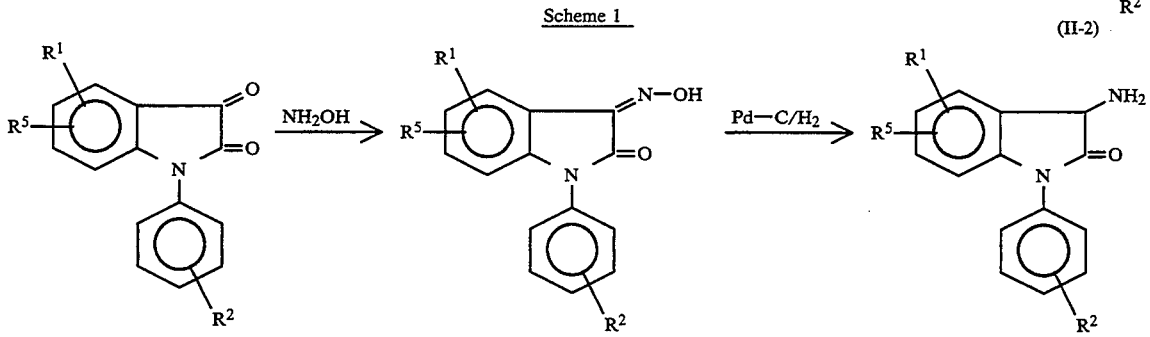

J. Parkt. Chem., 317,435 (1975)
J. Med. Chem., 33,2358 (1990)

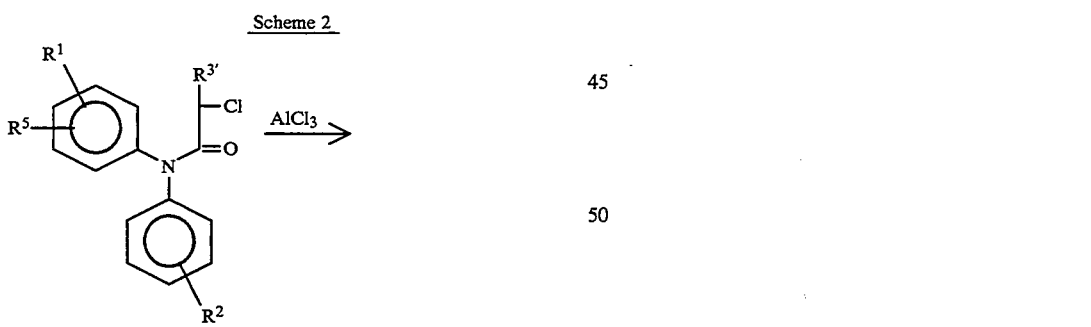

J. Med. Chem., 15, 762 (1972)

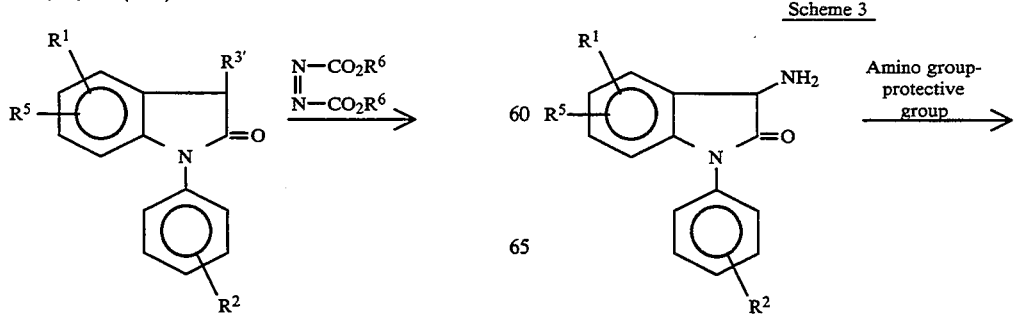

-continued
Scheme 3

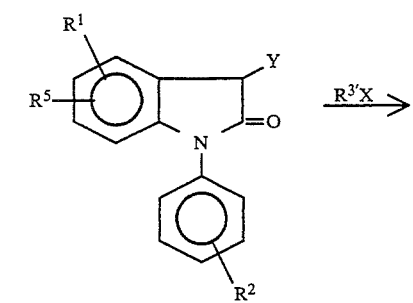

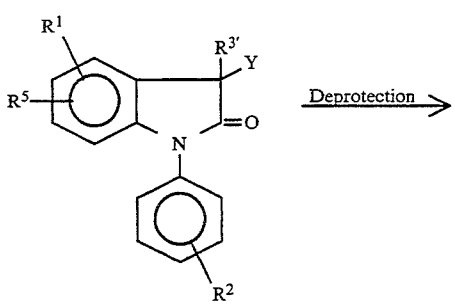

(II-2)

Scheme 4

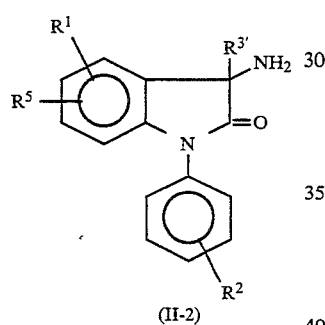

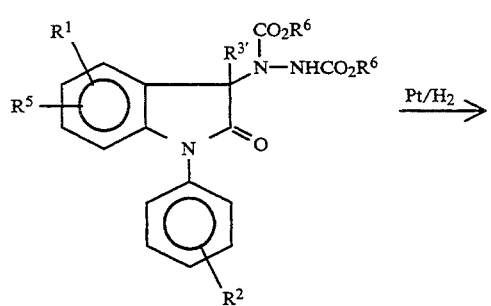

-continued
Scheme 4

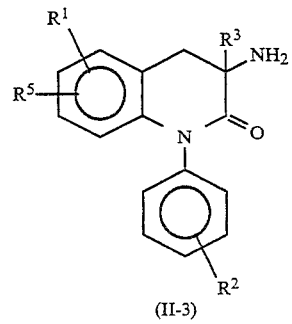

(II-3)

Scheme 5

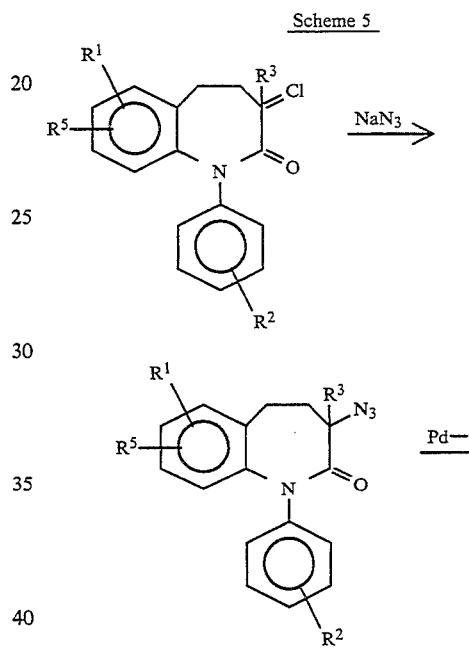

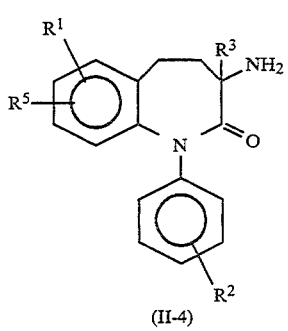

(II-4)

wherein R³' represents a lower alkyl group, a carboxy lower alkyl group or a lower alkoxycarbonyl lower alkyl group, R⁶ represents benzyl group or a tertiary butyl group, X represents a reactive residue, Y represents a protected amino group, and R¹, R², R³ and R⁵ have the same meanings as defined above.

The 3-carboxy-β-carboline represented by the formula (III) can be prepared according to M. Chain et al., J. Med. Chem., 25, 1081 (1982) and A. Huth et al., Arch. Pharm. (wein heim) 321, 297 (1988).

The optically active β-carboline derivative represented by the formula (I) can be prepared by reacting the optically active amine compound represented by the formula (II) (wherein $R^1$, $R^2$, $R^3$, $R^5$, n and * have the same meanings as defined above) or a salt thereof with the carboxylic acid compound represented by the formula (III) (wherein $R^4$ have the same meaning as defined above), a reactive derivative thereof or a salt thereof.

The optical isomer represented by the formula (II) can be obtained by forming a diastereomer salt from the optically inactive amino compound prepared according to the above Schemes 1 to 3, with an optical resolving agent according to a conventional method.

As the above resolving agent, there may be used a conventional resolving agent, for example, optically active dibenzoyl tartaric acid.

In the present specification, the lower alkyl group may include an alkyl group having 1 to 6 carbon atoms such as methyl, ethyl, propyl, isopropyl, butyl, isobutyl, a tertiary butyl, pentyl and hexyl, preferably an alkyl group having 1 to 4 carbon atoms, particularly preferably methyl group and ethyl group. The lower alkoxy group may include an alkoxy group having 1 to 6 carbon atoms such as methoxy, ethoxy, propoxy and butoxy, preferably an alkoxy group having 1 to 4 carbon atoms, particularly preferably methoxy group. The halogen atom may include chlorine, bromine, fluorine and iodine, preferably chlorine and fluorine. The lower alkanoyl group may include an alkanoyl group having 2 to 6 carbon atoms such as acetyl, propanoyl, butanoyl and hexanoyl, preferably an alkanoyl group having 2 to 4 carbon atoms, particularly preferably acetyl group. The lower alkylenedioxy group may include an alkylenedioxy group having 1 to 4 carbon atoms, particularly methylenedioxy group. The aryl group may include a phenyl group. The aralkyl group may include a benzyl group. The alkanesulfonyl group may include an alkanesulfonyl group having 1 to 6 carbon atoms, such as methanesulfonyl and ethanesulfonyl, preferably an alkanesulfonyl group having 1 to 4 carbon atoms.

EXAMPLES

The present invention is described in detail by referring to Reference examples and Examples, but the present invention is not limited by these Examples.

Example 1

3-{9H-pyrido [3,4-b]-indol-3-yl-carbonyl}-amino-1-(4-fluorophenyl)-5-methoxy-2-indolinone[=1-(4-fluorophenyl)-5-methoxy-3-{[(9H-pyrido[3,4-b]indol-3-yl)carbonyl]amino}-1H-indol-2(3H)-one]

In 40 ml of chloroform were dissolved 2.0 g (6.48 mole) of 3-amino-1-(4-fluorophenyl)-5-methoxy-2-ketoindoline hydrochloride and 2.4 g (1.2 equivalent) of β-carbolin-3-yl-carbonyl chloride, and to the solution was added dropwise a solution of 4 ml of triethylamine dissolved in 20 ml of chloroform under ice cooling and stirring. The reaction mixture was stirred for 3 hours and then poured into water. Insolubles precipitated were removed by filtration using celite and washed with chloroform. The chloroform layer was washed with water and then with a saline solution, and dried over anhydrous sodium sulfate. Thereafter, the solvent was removed under reduced pressure, and the residue was crystallized from a mixed solvent of ethyl acetate and chloroform (2:1 v/v) to obtain 2.34 g of the title compound as colorless crystals. Melting point: 220° to 223° C.

In the same manner, the following compounds were obtained from the corresponding starting materials.

Example 2

3-{9H-pyrido[3,4-b]-indol-3-yl-carbonyl}-amino-3-methyl-1-phenyl-2-indolinone
Melting point: 203° to 207° C.

Example 3

3-{9H-pyrido[3,4-b]-indol-3-yl-carbonyl}-amino-1-phenyl-2-indolinone
Melting point: 175° to 180° C.

Example 4

3-{9H-pyrido[3,4-b]-indol-3-yl-carbonyl}-amino-1-(2-fluorophenyl)-5,6-methylenedioxy-2-indolinone
Melting point: 253° to 256° C. (decomposed)

Example 5

3-{9H-pyrido[3,4-b]-indol-3-yl-carbonyl}-amino-1-(2-fluorophenyl)-2-indolinone
Melting point: 184° to 187° C. (decomposed)

Example 6

3-{9H-pyrido[3,4-b]-indol-3-yl-carbonyl}-amino-1-(4-fluorophenyl)-2-indolinone
Melting point: 201° to 205° C. (decomposed)

Example 7

3-{9H-pyrido[3,4-b]-indol-3-yl-carbonyl}-amino-1-(3-chlorophenyl)-2-indolinone
Melting point: 207° to 210° C. (decomposed)

Example 8

3-{9H-pyrido[3,4-b]-indol-3-yl-carbonyl}-amino-1-(2-fluorophenyl)-6-methoxy-2-indolinone
Melting point: 246° to 249° C. (decomposed)

Example 9

3-{9H-pyrido[3,4-b]-indol-3-yl-carbonyl}-amino-1-phenyl-5,6-methylenedioxy-2-indolinone
Melting point: 220° C. (decomposed)

Example 10

3-{9H-pyrido[3,4-b]-indol-3-yl-carbonyl}-amino-1-(2-fluorophenyl)-5-methoxy-2-indolinone
Melting point: 191° to 193° C.

Example 11

3-{9H-pyrido[3,4-b]-indol-3-yl-carbonyl}-amino-1-(4-methoxyphenyl)-2-indolinone
Melting point: 145° to 155° C. (decomposed)

Example 12

3-{9H-pyrido[3,4-b]-indol-3-yl-carbonyl}-amino-1-phenyl-6-methoxy-2-indolinone
Melting point: 172° to 175° C. (decomposed)

Example 13

3-{9H-pyrido[3,4-b]-indol-3-yl-carbonyl}-amino-1-phenyl-6-methyl-2-indolinone
Melting point: 262° to 265° C.

Example 14

3-{9H-pyrido[3,4-b]-indol-3-yl-carbonyl}-amino-1-(3-fluorophenyl)-2-indolinone
Melting point: 206° to 210° C.

Example 15

3-{9-acetyl-9H-pyrido[3,4-b]-indol-3-yl-carbonyl}-amino-1-(4-fluorophenyl)-5-methoxy-2-indolinone
Melting point: 201° to 204° C.

Example 16

3-{9-acetyl-9H-pyrido[3,4-b]-indol-3-yl-carbonyl}-amino-1-phenyl-2-indolinone
Melting point: 196° to 198° C.

Example 17

3-{9-methyl-9H-pyrido[3,4-b]-indol-3-yl-carbonyl}-amino-1-phenyl-2-indolinone
Melting point: 200° to 205° C.

Example 18

3-{9-methyl-9H-pyrido[3,4-b]-indol-3-yl-carbonyl}-amino-1-(4-fluorophenyl)-5-methoxy-2-indolinone
Melting point: 166° to 170° C.

Example 19

3-{9H-pyrido[3,4-b]-indol-3-yl-carbonyl}-amino-1-(4-fluorophenyl)-6-methoxy-2-indolinone
Melting point: 202° to 205° C.

Example 20

3-{9H-pyrido[3,4-b]-indol-3-yl-carbonyl}-amino-3-methyl-1-(4-fluorophenyl)-5-methoxy-2-indolinone
Melting point: 219° to 222° C.

Example 21

3-{9H-pyrido[3,4-b]-indol-3-yl-carbonyl}-amino-3-methyl-1-(2-fluorophenyl)-2-indolinone
Melting point: 189° to 191° C.

Example 22

3-{9H-pyrido[3,4-b]-indol-3-yl-carbonyl}-amino-1-phenyl-3,4-dihydroquinolin-2(1H)-one
Melting point: >300° C. IR (Nujol)(cm$^{-1}$): 3300, 2900, 1680, 1660 MS (m/z): 432 (M$^+$), 222 (base)

Example 23

3-{9H-pyrido[3,4-b]-indol-3-yl-carbonyl}-amino-3-ethyl-1-(4-fluorophenyl)-5-methoxy-2-indolinone
Colorless needle crystal Melting point: 203° to 204° C. IR (Nujol)(cm$^{-1}$): 3380, 3280, 1710, 1665, 1625 FAB-MS (m/z): 495 (MH$^+$)

Example 24

3-{9H-pyrido[3,4-b]-indol-3-yl-carbonyl}-amino-3-n-butyl-1-(4-fluorophenyl)-5-methoxy-2-indolinone
Colorless needle crystal Melting point: 209° to 210° C. IR (Nujol) (cm$^{-1}$): 3380, 3330, 1715, 1665, 1625 FAB-MS (m/z): 523 (MH$^+$)

Example 25

3-{9H-pyrido[3,4-b]-indol-3-yl-carbonyl}-amino-3-isopropyl-1-(4-fluorophenyl)-5-methoxy-2-indolinone
Colorless needle crystal Melting point: 197° to 197.5° C. IR (Nujol) (cm$^{-1}$): 3390, 3260, 1715, 1675, 1630 FAB-MS (m/z):509 (MH$^+$)

Example 26

3-{9H-pyrido[3,4-b]-indol-3-yl-carbonyl}-amino-1-phenyl-2,3,4,5-tetrahydro-1-benzoazepin-2(1H)-one In 15 ml of dimethylformamide were dissolved 0.252 g of 3-amino-1-phenyl-2,3,4,5-tetrahydro-1-benzoazepin-2(1H)-one, 0.127 g of 1-hydroxybenzotriazole, 0.223 g of 3-carboxy-β-carboline and 0.2 g of 1-ethyl-3-(3'-dimethylaminopropyl)-carbodiimide hydrochloride and 0.5 ml of triethylamine was added to the solution, and the mixture was stirred at room temperature for one day. After the solvent was removed under reduced pressure, a 10% aqueous citric acid and chloroform were added to the residue and the mixture was stirred. Thereafter, the chloroform layer was separated, washed with a 10% sodium hydroxide aqueous solution and then with water, and dried over anhydrous sodium sulfate. The solvent was removed under reduced pressure, and ethyl acetate was added to the residue. The precipitates were collected by filtration to obtain 0.312 g of the title compound as crystals. Melting point: 302° to 304° C., IR (Nujol) (cm$^{-1}$): 3360, 3290, 1730, 1670, 1650, 1625, MS (m/z): 446 (M$^+$), 264 (base)

Example 27

3-{9-acetyl-9H-pyrido[3,4-b]-indol-3-yl-carbonyl}-amino-3-methyl-1-phenyl-2-indolinone A mixture of 900 mg of 3-{9H-pyrido[3,4-b]-indol-3-yl-carbonyl}amino-3-methyl-1-phenyl-2-indolinone, 5 ml of anhydrous acetic acid and 5 ml of pyridine was stirred at 80° C. for 6 hours, After the reaction mixture was cooled to room temperature, a mixed solvent of ethyl acetate and hexane was added to the mixture. The precipitates were collected by filtration to obtain 720 mg of the title compound as colorless powder. Melting point: 279° to 280° C., IR (Nujol) (cm$^{-1}$): 3390, 1740, 1700, 1675, 1615, MS (m/z): 474 (M$^+$), 193 (base)

In the same manner as mentioned above, the following compounds were obtained from the corresponding starting materials.

Example 28

3-{9-acetyl-9H-pyrido[3,4-b]-indol-3-yl-carbonyl}-amino-3-methyl-1-(4-fluorophenyl)-5-methoxy-2-indolinone
Melting point: 165° to 171° C.

Example 29

3-{9-acetyl-9H-pyrido[3,4-b]-indol-3-yl-carbonyl}-amino-3-ethyl-1-(4-fluorophenyl)-5-methoxy-2-indolinone
Colorless fine needle crystal Melting point: 258° to 259° C. IR (Nujol) (cm$^{-1}$): 3390, 1720, 1700, 1670, 1620 FAB-MS (m/z): 537 (MH$^+$)

Example 30

3-{9-acetyl-9H-pyrido[3,4-b]-indol-3-yl-carbonyl}-amino-3-n-butyl-1-(4-fluorophenyl)-5-methoxy-2-indolinone
Colorless fine needle crystals Melting point: 151° to 158° C. IR (Nujol) (cm$^{-1}$): 3360, 1730, 1700, 1660, 1620 FAB-MS (m/z): 565 (MH$^+$)

Example 31

3-{9-acetyl-9H-pyrido[3,4-b]-indol-3-yl-carbonyl}-amino-3-isopropyl-1-(4-fluorophenyl)-5-methoxy-2-indolinone
Melting point: 239° to 240° C. IR (Nujol) (cm$^{-1}$): 3390, 3370, 1725, 1705, 1670, 1625 FAB-MS (m/z): 551 (MH$^+$)

Example 32

3-{9-acetyl-9H-pyrido[3,4-b]-indol-3-yl-carbonyl}-amino-5-hydroxy-1-(4-fluorophenyl)-2-indolinone In 40 ml of dichloromethane was suspended 1.54 g (3.04 mmole) of 3-{9-acetyl-9H-pyrido[3,4-b]-indol-3-yl-carbonyl}-amino-5-methoxy-1-(4-fluorophenyl)-2-indolinone, and to the suspension was added dropwise under ice cooling a solution of 1.1 ml (4 mole equivalent) of boron tribromide dissolved in 10 ml of dichloromethane. After completion of the dropwise addition, the mixture was stirred for 10 minutes under ice cooling and then stirred at room temperature for 1.5 hours. After completion of the reaction, the reaction mixture was treated with methanol under ice cooling, and then the solvent was removed under reduced pressure. Methanol was added to the residue, and the precipitates were collected by filtration to obtain 1.07 g of a hydrobromide of the title compound as pale yellow crystals. Melting point: 239° to 241° C., IR (Nujol) (cm$^{-1}$): 1720, 1680, FAB-MS (m/z): 495 (MH$^+$, base)

In the same manner as mentioned above, the following compound was obtained from the corresponding starting materials.

Example 33

3-{9H-pyrido[3,4-b]-indol-3-yl-carbonyl}-amino-5-hydroxy-1-(4-fluorophenyl)-2-indolinone Melting point: 274° to 276° C.

Example 34

3-{9-acetyl-9H-pyrido[3,4-b]-indol-3-yl-carbonyl}-amino-3-methyl-1-phenyl-2-indolinone A mixture of 0.432 g of the compound obtained in Example 16, 0.414 g of potassium carbonate, 0.185 g of methyl iodide and 15 ml of acetone was stirred at room temperature overnight. The solvent was removed under reduced pressure, and water was added to the residue. The precipitates were collected by filtration and washed with ethyl acetate to obtain 0.32 g of the title compound. Physical data of the present compound were identical with those of the compound obtained in Example 27.

Example 35

3-{(9-acetyl-9H-pyrido[3,4-b]-indol-3-yl-carbonyl)amino}-3-(2-methoxycarbonylethyl)-1-phenyl-2-indolinone A mixture of 0.627 g of the compound obtained in Example 16, 0.586 g of methyl acrylate, 0.375 g of potassium carbonate and 12 ml of acetone was stirred under argon atmosphere at room temperature overnight. After removing the solvent under reduced pressure, water was added to the residue and the mixture was extracted with chloroform. The chloroform layer was dried and then evaporated to dryness under reduced pressure, and the residue was purified by silica gel column chromatography (solvent; chloroform:ethyl acetate =3:1 (v/v)) and recrystallized from a mixed solution of ethyl acetate and ether to obtain 0.615 g of the title compound as colorless needle crystals. Melting point: 189° to 192° C., IR (Nujol) (cm$^{-1}$): 3400, 1745, 1735, 1700, 1675, 1615

Example 36

3-{9-(2-methoxycarbonylethyl)-9H-pyrido[3,4-b]-indol-3-yl-carbonyl)amino}-3-(2-methoxycarbonylethyl)-1-phenyl-2-indolinone By treating the compound obtained in Example 3 in the same manner as in Example 35 (except for effecting reaction for 3 days), the title compound was obtained as an oily product.

Example 37

3-{9-(2-methoxycarbonylethyl)-9H-pyrido[3,4-b]-indol-3-yl-carbonyl)amino}-3-(2-methoxycarbonylethyl)-1-(4-fluorophenyl)-5-methoxy-2-indolinone By treating the compound obtained in Example 1 in the same manner as in Example 35 (except for effecting reaction for 3 days), the title compound was obtained as colorless prism crystals. Melting point: 128° to 130° C., IR (Nujol) (cm$^{-1}$): 3360, 1740, 1720, 1640

Example 38

3-{9H-pyrido[3,4-b]-indol-3-yl-carbonyl}-amino-3-methyl-1-phenyl-2-indolinone

A mixed solution of 0.474 g of the compound obtained in Example 34, 1.5 ml of 2N—NaOH, 10 ml of methanol and 5 ml of tetrahydrofuran was stirred at room temperature overnight. After removing the solvent under reduced pressure, water was added to the residue and the mixture was extracted with chloroform. The chloroform layer was washed with water, dried and then solidified under reduced pressure. The residue was recrystallized from ethyl acetate-hexane to obtain 0.38 g of the title compound as colorless needle crystals. Physical data of the present compound were identical with those of the compound obtained in Example 2.

Example 39

3-{9H-pyrido[3,4-b]-indol-3-yl-carbonyl}amino}-3-(2-carboxyethyl)-1-phenyl-2-indolinone (hydrochloride)

By treating the compound obtained in Example 35 in the same manner as in Example 38, the title compound was obtained as pale yellow powder. Melting point: 230° C. (decomposed), IR (Nujol) (cm$^{-1}$): 3320, 1715, 1680, 1640, 1610, FAB-MS (m/z): 491 (MH$^+$)

Example 40

3-{9-(2-carboxyethyl)-9H-pyrido[3,4-b]-indol-3-yl-carbonyl}-amino-3-(2-carboxyethyl)-1-phenyl-2-indolinone By treating the compound obtained in Example 36 in the same manner as in Example 38, the title compound was obtained as colorless powder. Melting point: 219° to 222° C., IR (Nujol) (cm$^{-1}$): 3360, 1720, 1705, 1645, 1610, FAB-MS (m/z): 563 (MH$^+$)

Example 41

3-{9H-pyrido[3,4-b]-indol-3-yl-carbonyl}-amino-3-ethoxycarbonylmethyl-1-phenyl-2-indolinone (1) A mixed solution of 3.54 g of 1-phenyl-3-(1,3-dioxoisoindolin-2-yl)-2,3-dihydro-1H-indol-2-one, 8.4 g of ethyl bromoacetate, 2.76 g of potassium carbonate and 40 ml of acetone was stirred under argon atmosphere at room temperature overnight. After removing the solvent, water was added to the residue and the mixture was extracted with ethyl acetate. The ethyl acetate layer was washed and dried, and then the solvent was removed under reduced pressure. The residue was purified by silica gel column chromatography (solvent; chloroform:ethanol=40:1 (v.v)) and recrystallized from ether to obtain 2.20 g of 1-phenyl-3-(ethoxycarbonylmethyl)-3-(1,3-dioxoisoindolin-2-yl)-2,3-dihydro-1H-indol-2-one as colorless prism crystals. Melting point: 148° to 149° C., IR (Nujol) (cm$^{-1}$): 1780, 1740, 1720, 1610, MS (DI, m/z): 440 (M$^+$)

(2) To a mixed solution of 1.44 g of the compound obtained in the above (1), 10 ml of methanol and 10 ml of tetrahydrofuran was added 0.19 g of a hydrazine hydrate, and the mixture was stirred at room temperature overnight. Then, after the mixture was refluxed for 24 hours, the solvent was removed. The residue was purified by silica gel column chromatography (solvent; chloroform:ethanol=20:1 (v/v)) to obtain 1-phenyl-3-ethoxycarbonylmethyl-3-amino-2,3-dihydro-1H-indol-2-one as an oily product. To the resulting product were added 4 ml of triethylamine and 21 ml of chloroform, and further 1.07 g of β-carbolin-3-yl-carbonyl chloride.hydrochloride under ice cooling, and the mixture was stirred overnight. After adding water to the reaction mixture, the mixture was extracted with chloroform. The chloroform layer was washed, dried and then evaporated to obtain the title compound as a caramel-like product. IR (Nujol) (cm$^{-1}$): 3280, 1730, 1720, 1670, 1610, MS (DI, m/z): 504 (M+)

Example 42

In the same manner as in Example 41, the following compound was obtained from the corresponding starting materials.

3-{9H-pyrido[3,4-b]-indol-3-yl-carbonyl}-amino-3-methoxycarbonylmethyl-1-(4-fluorophenyl)-5-methoxy-2-indolinone Melting point: 170° to 172° C., IR (Nujol) (cm$^{-1}$): 3380, 3280, 1740, 1720, 1670, 1660, FAB-MS (m/z): 539 (MH+)

Examples 43 and 44

By treating the compounds obtained in Examples 41 and 42 in the same manner as in Example 38, the following compounds were obtained.

(43) 3-{9H-pyrido[3, 4-b]-indol-3-yl-carbonyl }-amino-3-carboxymethyl-1-phenyl-2-indolinone Melting point: 300° to 302° C. IR (Nujol) (cm$^{-1}$): 3352, 3300, 1740, 1700, 1620 MS (DI, m/z): 476 (M+)

(44) 3-{9H-pyrido[3,4-b]-indol-3-yl-carbonyl}-amino-3-carboxymethyl-1-(4-fluorophenyl)-5-methoxy-2-indolinone (sodium salt)

Melting point: 252° to 255° C. (decomposed) IR (Nujol) (cm$^{-1}$): 3280, 1705, 1665, 1630, 1600 FAB-MS (m/z): 569 (MNa+), 547 (MH+)

Example 45

(S)-3-{9H-pyrido[3,4-b]-indol-3-yl-carbonyl}-amino-3-methyl-1-(4-fluorophenyl)-5-methoxy-2-indolinone In the same manner as in Example 1, the title compound was obtained from (S) -3-amino-3-methyl-1-(4-fluorophenyl)-5-methoxy-2,3-dihydro-1H-indol-2-one and β-carbolin-3-yl-carbonyl chloride. Melting point: 231° to 233° C., [α]$_D^{25}$: +62.1° (c=0.58, CHCl$_3$)

In the same manner as mentioned above, the following compounds were obtained from the corresponding starting materials.

Example 46

(R)-3-{9H-pyrido[3,4-b]-indol-3-yl-carbonyl}-amino-3-methyl-1-(4-fluorophenyl)-5-methoxy-2-indolinone Melting point: 231° to 233° C. [α]$_D^{25}$: −62.93° (c=0.63, CHCl$_3$)

Example 47

(S)-3-{9H-pyrido[3,4-b]-indol-3-yl-carbonyl}-amino-3-methyl-1-(2-fluorophenyl)-2-indolinone.methanesulfonate Melting point: 287° to 289° C. [α]$_D^{25}$: +214.3° (c=0.446, MeOH)

Example 48

(R)-3-{9H-pyrido[3,4-b]-indol-3-yl-carbonyl}-amino-3-methyl-1-(2-fluorophenyl)-2-indolinone.methanesulfonate Melting point: 289° to 290° C. [α]$_D^{25}$: −210.7° (c=0.430, MeOH)

Example 49

(+)-3-{9H-pyrido[3, 4-b]-indol-3-yl-carbonyl}-amino-3-methyl-1-phenyl-2-indolinone Melting point: 205° to 207° C. [α]$_D^{20}$: +139.2° (c=0.241, CHCl$_3$) hydrochloride Melting point: 236° C.

Example 50

(−)-3-{9H-pyrido[3,4-b]-indol-3-yl-carbonyl}-amino-3-methyl-1-phenyl-2-indolinone Melting point: 205° to 207° C. [α]$_D^{20}$: −139.65° (c=0.232, CHCl$_3$)

Example 51

(S)-3-{9-methyl-9H-pyrido[3,4-b]-indol-3-yl-carbonyl}-amino-3-methyl-1-(4-fluorophenyl)-5-methoxy-2-indolinone A mixture of 0.55 g of (S)-3-{9H-pyrido[3,4-b]-indol-3-yl-carbonyl}-amino-3-methyl-1-(4-fluorophenyl)-5-methoxy-2-indolinone, 0.2 ml of methyl iodide, 0.78 g of potassium carbonate and 10 ml of dimethylformamide was stirred at room temperature for 3 hours, and water and ethyl acetate were added to the mixture. The organic layer was separated, washed, dried, and evaporated under reduced pressure. The residue was crystallized from a mixed solvent of hexane and ethyl acetate to afford 0.403 g of the title compound as pale yellow crystals. Melting point: 232° to 233° C., [α]$_D^{20}$: 0° (c=0.214, CHCl$_3$)

The above alkylating reaction can be preferably carried out by using alkyl halides such as ethyl iodide, butyl iodide and butyl chloride.

In the same manner, the following compounds were obtained from corresponding starting materials and the alkylating agent, acylating agent and sulfonating agent described below.

Example 52

(S)-3-{9-phenylcarbonyl-9H-pyrido[3,4-b]-indol-3-yl-carbonyl}-amino-3-methyl-1-(4-fluorophenyl)-5-methoxy-2-indolinone (from benzoyl chloride)

Melting point: 183° to 185° C. [α]$_D^{20}$: +66.35° (c=0.214, CHCl$_3$)

Example 53

(S)-3-{9-methylsulfonyl-9H-pyrido[3,4-b]-indol-3-yl-carbonyl}-amino-3-methyl-1-(4-fluorophenyl)-5-methoxy-2-indolinone (from methylsulfonyl chloride)

Melting point: 213° to 215° C. [α]$_D^{20}$: +102.01° (c=0.298, CHCl$_3$)

Example 54

(S)-3-{9-ethylcarbonyl-9H-pyrido[3,4-b]-indol-3-yl-carbonyl}-amino-3-methyl-1-(4-fluorophenyl)-5-methoxy-2-indolinone (from propionic anhydride)

Melting point: 164° to 167° C. [α]$_D^{20}$: +54.73° (c=0.380, CHCl$_3$)

Example 55

(S)-3-{9-ethyl-9H-pyrido[3,4-b]-indol-3-yl-carbonyl}-amino-3-methyl-1-(4-fluorophenyl)-5-methoxy-2-indolinone (from ethyl iodide)

Melting point: 219° C. $[\alpha]_D^{20}$: +10.32° (c=0.368, CHCl$_3$)

Example 56

(S)-3-{9-n-butyl-9H-pyrido[3,4-b]-indol-3-yl-carbonyl}-amino-3-methyl-1-(4-fluorophenyl)-5-methoxy-2-indolinone (from butyl iodide)

Amorphous solid, $[\alpha]_D^{20}$: +11.94° (c=0.318, CHCl$_3$)

Example 57

(S)-3-{9-methoxycarbonyl-9H-pyrido[3,4-b]-indol-3-yl-carbonyl}-amino-3-methyl-1-(4-fluorophenyl)-5-methoxy-2-indolinone (from methoxycarbonyl chloride)

Melting point: 175° to 176° C. $[\alpha]_D^{20}$: +49.18° (c=0.370, CHCl$_3$)

Example 58

(S)-3-{9-benzyl-9H-pyrido[3,4-b]-indol-3-yl-carbonyl}-amino-3-methyl-1-(4-fluorophenyl)-5-methoxy-2-indolinone (from benzyl chloride)

Amorphous solid, $[\alpha]_D^{20}$: +22.96° (c=0.418, CHCl$_3$)

Example 59

(S)-3-{9-i-propylcarbonyl-9H-pyrido[3,4-b]-indol-3-yl-carbonyl}-amino-3-methyl-1-(4-fluorophenyl)5-methoxy-2-indolinone (from isobutyric acid chloride)

Melting point: 224.2° to 224.4° C. $[\alpha]_D^{20}$: +58.15° (c=0.368, CHCl$_3$)

Example 60

(S)-3-{9-formyl-9H-pyrido[3,4-b]-indol-3-yl-carbonyl}-amino-3-methyl-1-(4-fluorophenyl)-5-methoxy-2-indolinone Melting point: 179° to 185° C. $[\alpha]_D^{25}$: +60.66° (c=0.300, CHCl$_3$)

Example 61

(S)-3-{9-isopropyl-9H-pyrido[3,4-b]-indol-3-yl-carbonyl}-amino-3-methyl-1-(4-fluorophenyl)-5-methoxy-2-indolinone Melting point: 137° to 138.5° C. $[\alpha]_D^{20}$: +9.32° (c=0.236, CHCl$_3$)

Example 62

(S)-3-{9-methoxycarbonylmethyl-9H-pyrido[3,4-b]-indol-3-yl-carbonyl}-amino-3-methyl-1-(4-fluorophenyl)-5-methoxy-2-indolinone hydrochloride Melting point: ~169° C. $[\alpha]_D^{20}$: +92.95° (c=0.284, CHCl$_3$)

Example 63

(S)-3-{9-carboxymethyl-9H-pyrido[3,4-b]-indol-3-yl-carbonyl}-amino-3-methyl-1-(4-fluorophenyl)-5-methoxy-2-indolinone.sodium salt Melting point: >300° C. $[\alpha]_D^{20}$: +10.66° (c=0.150, MeOH)

Example 64

(S)-3-{9-dimethylaminosulfonyl-9H-pyrido[3,4-b]-indol-3-yl-carbonyl}-amino-3-methyl-1-(4-fluorophenyl)-5-methoxy-2-indolinone.hydrochloride Melting point: ~230° C. $[\alpha]_D^{20}$: +49.29° (c=0,264, MeOH)

Example 65

(S)-3-{9-acetyl-9H-pyrido[3,4-b]-indol-3-yl-carbonyl}-amino-3-methyl-1-(4-fluorophenyl)-5-methoxy-2-indolinone (from acetic anhydride)

Melting point: 201° to 202.5° C. $[\alpha]_D^{25}$: +57.1° (c=0.834, CHCl$_3$)

Example 66

(R)-3-{9-acetyl-9H-pyrido[3,4-b]-indol-3-yl-carbonyl}-amino-3-methyl-1-(4-fluorophenyl)-5-methoxy-2-indolinone (from acetic anhydride)

Melting point: 203.5° to 205° C. $[\alpha]_D^{25}$: −57.2° (c=0.874, CHCl$_3$)

Example 67

(S)-3-{9-acetyl-9H-pyrido[3,4-b]-indol-3-yl-carbonyl}-amino-3-methyl-1-(2-fluorophenyl)-2-indolinone Melting point: 180° to 181° C. $[\alpha]_D^{25}$: +135.83° (c=0.480, CHCl$_3$)

Example 68

(S)-3-{9-isopropylcarbonyl-9H-pyrido[3,4-b]-indol-3-yl-carbonyl}-amino-3-methyl-1-(2-fluorophenyl)-2-indolinone (from isobutyryl chloride)

Melting point: 150° to 153° C. $[\alpha]_D^{25}$: +121.56° (c=0.408, CHCl$_3$)

Example 69

(S)-3-{9-ethyl-9H-pyrido[3,4-b]-indol-3-yl-carbonyl}-amino-3-methyl-1-(2-fluorophenyl)-2-indolinone methanesulfonate (from ethyl iodide)

Amorphous solid, $[\alpha]_D^{25}$: +118.14° (c=0.452, CHCl$_3$)

Example 70

(S)-3-{9-n-butyl-9H-pyrido[3,4-b]-indol-3-yl-carbonyl}-amino-3-methyl-1-(2-fluorophenyl)-2-indolinone hydrochloride (from butyl iodide)

Melting point: 221° to 223° C. $[\alpha]_D^{25}$: +127.17° (c=0.574, CHCl$_3$)

Example 71

(S)-3-{9-methoxycarbonyl-9H-pyrido[3,4-b]-indol-3-yl-carbonyl}-amino-3-methyl-1-(2-fluorophenyl)-2-indolinone (from methoxycarbonyl chloride)

Amorphous solid, $[\alpha]_D^{25}$: +122.96° (c=0.418, CHCl$_3$)

Example 72

(S)-3-{9-dimethylaminosulfonyl-9H-pyrido[3,4-b]-indol-3-yl-carbonyl}-amino-3-methyl-1-(2-fluorophenyl)-2-indolinone (from dimethylaminosulfonyl chloride)

Melting point: 275° to 277° C. $[\alpha]_D^{25}$: +103.57° (c=0.280, CHCl$_3$)

Example 73

(S)-3-{9-methoxycarbonylmethyl-9H-pyrido[3,4-b]-indol-3-yl-carbonyl}-amino-3-methyl-1-(2-fluorophenyl)2-indolinone (from methyl bromoacetate)

Amorphous solid, $[\alpha]_D^{25}$: +95.07° (c=0.528, CHCl$_3$)

Example 74

(S)-3-{9-carboxymethyl-9H-pyrido[3,4-b]-indol-3-yl-carbonyl}-amino-3-methyl-1-(2-fluorophenyl)-2-indolinone By treating the compound obtained in Example 73 in the same manner as in Example 38, the title compound was obtained.

Melting point: 179° to 180° C. $[\alpha]_D^{25}$: +135.00° (c=0.320, CHCl$_3$)

Example 75

(−)-3-{9-acetyl-9H-pyrido[3,4-b]-indol-3-yl-carbonyl}-amino-3-methyl-1-phenyl-2-indolinone (from acetic anhydride)

Melting point: 174° to 176° C. $[\alpha]_D^{20}$: −122.13° (c=0.244, CHCl$_3$)

Example 76

(+)-3-{9-acetyl-9H-pyrido[3,4-b]-indol-3-yl-carbonyl}-amino-3-methyl-1-phenyl-2-indolinone (from acetic anhydride)

Melting point: 188° C. $[\alpha]_D^{20}$: +121.42° (c=0.224, CHCl$_3$)

Example 77

(+)-3-{9-methylsulfonyl-9H-pyrido[3,4-b]-indol-3-yl-carbonyl}-amino-3-methyl-1-phenyl-2-indolinone (from methylsulfonyl chloride)

Melting point: 180° C. $[\alpha]_D^{20}$: +91.42° (c=0.210, CHCl$_3$)

Example 78

(+)-3-{9-methyl-9H-pyrido[3,4-b]-indol-3-yl-carbonyl}-amino-3-methyl-1-phenyl-2-indolinone hydrochloride (from methyl iodide)

Melting point: 217° C. $[\alpha]_D^{20}$: +196.26° (c=0.214, CHCl$_3$)

Example 79

(+)-3-{9-isopropyl-9H-pyrido[3,4-b]-indol-3-yl-carbonyl}-amino-3-methyl-1-phenyl-2-indolinone (from isopropyl iodide)

Melting point: 214° C. $[\alpha]_D^{20}$: +178.12° (c=0.256, CHCl$_3$)

Example 80

In the same manner as in Example 1, the following compound was obtained from the corresponding starting materials.

3-{9-acetyl-9H-pyrido[3,4-b]-indol-3-yl-carbonyl}-amino-3-methyl-1-(4-fluorophenyl)-6-methoxy-2-indolinone Melting point: 180° to 183° C., MS (m/z): 522 (M+)

Example 81

In the same manner as in Example 1, the following compound was obtained from the corresponding starting materials.

3-{9H-pyrido[3,4-b]-indol-3-yl-carbonyl}-amino-3-methyl-1-(2-fluorophenyl)-6-methoxy-2-indolinone (methanesulfonate)

Melting point: 232° to 234° C., MS (m/z): 480 (M+)

Example 82

In the same manner as in Example 1, the following compound was obtained from the corresponding starting materials.

3-{9H-pyrido[3,4-b]-indol-3-yl-carbonyl}-amino-3-methyl-1-(3-chlorophenyl)-6-methoxy-2-indolinone (methanesulfonate)

Melting point: 170° to 180° C., MS (m/z): 497 (M+)

Example 83

By treating the compound obtained in Example 80 in the same manner as in Example 38, the following compound was obtained.

3-{9H-pyrido[3,4-b]-indol-3-yl-carbonyl}-amino-3-methyl-1-(4-fluorophenyl)-6-methoxy-2-indolinone Melting point: 199° to 201° C., MS (m/z): 480 (M+)

Example 84

In the same manner as in Example 27, the following compound was obtained from the corresponding starting materials.

3-{9-acetyl-9H-pyrido[3,4-b]-indol-3-yl-carbonyl}-amino-3-methyl-1-(2-fluorophenyl)-6-methoxy-2-indolinone Melting point: 172° to 174° C., MS (m/z): 522 (M+)

Example 85

In the same manner as in Example 27, the following compound was obtained from the corresponding starting materials.

3-{9-acetyl-9H-pyrido[3,4-b]-indol-3-yl-carbonyl}-amino-3-methyl-1-(3-chlorophenyl)-6-methoxy-2-indolinone Melting point: 158° to 160° C., MS (m/z): 539 (M+)

Reference Example 1

1-(4-fluorophenyl)-5-methoxy-1H-indol-2,3-dione

To a solution of 65 ml (0.745 mole) of oxalyl chloride dissolved in 65 ml of dichloromethane was added dropwise under ice cooling and stirring a solution of 32.3 g (0.149 mole) of 4-methoxy-4'-fluorodiphenylamine dissolved in 120 ml of dichloromethane, and the mixture was stirred under cooling for 1.5 hours. After completion of the reaction, the solvent was removed under reduced pressure, and 120 ml of dichloromethane was added to the residue. To the mixture was added 23.9 g (0.179 mole) of aluminum chloride under ice cooling, and the mixture was stirred at room temperature overnight. After completion of the reaction, the reaction mixture was treated with 10% hydrochloric acid, and the crystals precipitated were collected by filtration, washed with water and then with diethyl ether, and dried to obtain 38.7 g of the title compound as red crystals. Melting point: 246° to 247° C.

Reference Example 2

1-(4-fluorophenyl)-5-methoxy-1H-indol-2,3-dione-3-oxime

A mixture of 13.55 g (0.05 mole) of the isatin derivative obtained in the above Reference example 1, 10.43 g (0.15 mole) of hydroxyamine hydrochloride, 7.95 g (0.075 mole) of sodium carbonate, 500 ml of ethanol and 200 ml of water was refluxed for one hour. After completion of the reaction, ethanol was removed under reduced pressure, water was added to the residue, and the crystals precipitated were collected by filtration. The crystals obtained were washed with water and dried to obtain 14.3 g of the title compound as yellow crystals. Melting point: 217° to 219° C.

Reference Example 3

3-amino-1-(4-fluorophenyl)-5-methoxy-2,3-dihydro-1H-indol-2-one [=3-amino-1-(4-fluorophenyl)-5-methoxy-1H-indol-2(3H)-one]

A mixture of 14.3 g (0.05 mole) of the oxime obtained in the above Reference example 2, 8.2 ml of conc. hydrochloric acid, 3.0 g of 10% palladium-carbon and 500 ml of ethanol was subjected to catalytic reduction at room temperature under hydrogen atmosphere overnight. After completion of the reduction, the catalyst was removed by filtration and the solvent was removed under reduced pressure. The residue was crystallized from a mixed solvent of acetone and diethyl ether to obtain 12.4 g of a hydrochloride of the title compound as colorless crystals. Melting point: 170° to 175° C. (decomposed), IR (Nujol) (cm$^{-1}$): 1740, MS (DI, m/z): 272 (M$^+$)

In the same manner as mentioned above, the following compounds were obtained from corresponding starting materials.

Reference Example 4

3-amino-1-(2-fluorophenyl)-2,3-dihydro-1H-indol-2-one hydrochloride, Melting point: 182° to 183° C.

Reference Example 5

3-amino-1-phenyl-2,3-dihydro-1H-indol-2-one hydrochloride, Melting point: 90° C.

Reference Example 6

3-amino-1-(3-fluorophenyl)-2,3-dihydro-1H-indol-2-one hydrochloride, Melting point: 170° to 175° C. (decomposed)

Reference Example 7

3-amino-1-(4-fluorophenyl)-2,3-dihydro-1H-indol-2-one hydrochloride, Melting point: 162° C. (decomposed)

Reference Example 8

3-amino-1-(4-methoxyphenyl )-2,3-dihydro-1H-indol-2-one hydrochloride, Melting point: 145° to 155° C. (decomposed)

Reference Example 9

3-amino-1-(3-chlorophenyl)-2,3-dihydro-1H-indol-2-one hydrochloride, Melting point: 183° to 186° C. (decomposed)

Reference Example 10

3-amino-1-(4-fluorophenyl)-5-methyl-2,3-dihydro-1H-indol-2-one hydrochloride, Melting point: 170° to 175° C.

Reference Example 11

3-amino-1-phenyl-6-methyl-2,3-dihydro-1H-indol-2-one hydrochloride, Melting point: 168° to 178° C. (decomposed)

Reference Example 12

3-amino-1-(2-fluorophenyl)-6-methoxy-2,3-dihydro-1H-indol-2-one hydrochloride, Melting point: 160° to 161° C. (decomposed)

Reference Example 13

3-amino-1-phenyl-6-methoxy-2,3-dihydro-1H-indol-2-one hydrochloride, Melting point: 172° to 175° C. (decomposed)

Reference Example 14

3-amino-1-(4-fluorophenyl)-6-methoxy-2,3-dihydro-1H-indol-2-one hydrochloride, Melting point: 180° C. (decomposed)

Reference Example 15

3-amino-1-(2-fluorophenyl)-5-methoxy-2,3-dihydro-1H-indol-2-one hydrochloride, Melting point: 175° to 178° C. (decomposed)

Reference Example 16

3-amino-1-(2-fluorophenyl)-5,6-methylenedioxy-2,3-dihydro-1H-indol-2-one hydrochloride, Melting point: 176° to 178° C. (decomposed)

Reference Example 17

3-amino-1-phenyl-5,6-methylenedioxy-2,3-dihydro-1H-indol-2-one hydrochloride, Melting point: 183° to 186° C. (decomposed)

Reference Example 18

3-methyl-1-phenyl-2,3-dihydro-1H-indol-2-one

A mixture of 13.3 g (0.00513 mole) of N-(2-chloropropanoyl)-diphenylamine and 14.7 g (0.011 mole) of anhydrous aluminum chloride was stirred for 10 minutes while heating over an oil bath of 190° C. The reaction mixture was poured into 10% hydrochloric acid-ice, and the mixture was extracted with ethyl acetate. The ethyl acetate layer was washed successively with 10% hydrochloric acid, water, a sodium hydrogen carbonate aqueous solution and then water, and dried over anhydrous sodium sulfate. Ethyl acetate was removed under reduced pressure, and the residue was purified by silica gel column chromatography (eluent:ethyl acetate:hexane (1:5 (v.v))) and then recrystallized from hexane to obtain 9.54 g of the title compound as pale yellow crystals. Melting point: 77° to 78° C.

Reference Example 19

1,2-di(benzyloxycarbonyl)-1-(2,3-dihydro-3-methyl-1-phenyl-2-oxo-1H-indol-3-yl)-hydrazine After 8.5 g (0.00385 mole) of the indolinone derivative obtained in the above Reference example 18 were dissolved in 60 ml of dimethylformamide and 1.92 g (0.00502 mole) of sodium hydride (a 62.7% mineral oil dispersion) were added to the solution under argon atmosphere under ice cooling, the mixture was stirred at 5° C. for 20 minutes. Next, to the mixture was added 13.6 g of dibenzyl azodicarboxylate, and the mixture was stirred at room temperature for 30 minutes. After completion of the reaction, the reaction mixture was poured into aqueous ammonia-ice, and the mixture was extracted with ethyl acetate. The ethyl acetate layer was washed with water and then with a saline solution, and dried over anhydrous sodium sulfate. Ethyl acetate was removed under reduced pressure, and the residue was purified by silica gel column chromatography (eluent:ethyl acetate:hexane (1:3 to 1:1 v/v)) to obtain 20.4 g of the title compound as a colorless caramel-like product. MS (DI, m/z): 239 (M$^+$)

Reference Example 20

3-amino-3-methyl-1-phenyl-2,3-dihydro-1H-indol-2-one

A mixture of 3.26 g (0.00626 mole) of the hydrazine derivative obtained in the above Reference example 19, 0.7 ml of conc. hydrochloric acid, 0.2 g of a platinum oxide catalyst and 75 ml of methanol was subjected to catalytic reduction at room temperature under hydrogen atmosphere for 3 days. After completion of the reduction, the catalyst was removed by filtration and the filtrate was evaporated under reduced pressure. The residue was diluted with water and then washed with ethyl ether. The aqueous layer was made alkaline with a sodium hydrogen carbonate aqueous solution and then extracted with ethyl acetate. Next, the ethyl acetate layer was washed with water and dried over anhydrous sodium sulfate, and ethyl acetate was removed under reduced pressure. The residue was poured into methanol containing hydrogen chloride to obtain a hydrochloride. The hydrochloride was recrystallized from a mixed solvent of methanol and diethyl ether to obtain 1.00 g of a hydrochloride of the title compound as colorless crystals. Melting point: 268° to 269.5° C. (decomposed), MS (DI, m/z): 238 (M+)

Reference Example 21

5-methoxy-1-(4-fluorophenyl)-3-(1,2-dihydro-1,3-dioxoiso-1H-indol-2-yl)-2,3-dihydro-1H-indol-2-one In 80 ml of anhydrous dichloroethane was suspended 4.00 g (0.0013 mole) of 3-amino-1-(4-fluorophenyl)-5-methoxy-2,3-dihydro-1H-indol-2-one hydrochloride, and to the suspension was added 2.69 g (0.0182 mole, 1.4 equivalent) of phthalic anhydride at one time under argon atmosphere. Then, to the mixture was added 2 ml (0.00143 mole) of triethylamine over 10 minutes, and the mixture was stirred at room temperature for 10 minutes and then refluxed overnight. To the mixture were added 2 ml of triethylamine and 2 ml of methanol, and the mixture was refluxed for 20 minutes to decompose excessive phthalic anhydride. The reaction mixture was concentrated under reduced pressure and then extracted with ethyl acetate. The ethyl acetate layer was washed successively with a saturated sodium hydrogen carbonate aqueous solution, water, and then a saturated saline solution, and dried over anhydrous sodium sulfate. Ethyl acetate was removed under reduced pressure, and the residue was recrystallized from a mixed solvent of hexane and ethyl acetate to obtain 4.50 g of the title compound as colorless crystals. Melting point: 208.5° to 210.0° C., IR (Nujol) (cm$^{-1}$): 1730, 1715, 1495, 1400, 1225, 1210, 750, 715, MS (DI, m/z): 402 (M+, base), 227, 184, 76

Reference Example 22

5-methoxy-1-(4-fluorophenyl)-3-(benzyloxycarbonylamino)-2,3-dihydro-1H-indol-2-one A mixture of 30.0 g (0.0972 mole) of 3-amino-1-(4-fluorophenyl)-5-methoxy-2,3-dihydro-1H-indol-2-one hydrochloride, 18.2 g of benzyloxycarbonyl chloride, 200 ml of anhydrous dichloroethane and 200 ml of water was cooled in an ice-salt bath, and to the mixture was added 27.0 g of sodium hydrogen carbonate over 10 minutes under argon atmosphere while stirring. After the mixture was stirred at the same temperature for 20 minutes and at the room temperature for 20 minutes, the reaction mixture was washed with a 10% hydrochloric acid aqueous solution, water and then a saturated saline solution, and dried over anhydrous sodium sulfate. The solvent was removed under reduced pressure, and the residue was recrystallized from a mixed solvent of hexane and ethyl acetate to obtain 37.1 g of the title compound as colorless needle crystals. Melting point: 154.5° to 156° C.

Reference Example 23

5-methoxy-1-(4-fluorophenyl)-3-methyl-3-(1,2-dihydro-1,3-dioxoiso-1H-indol-2-yl)-2,3-dihydro-1H-indol-2-one To a solution of 4.50 g (0.0112 mole) of the phthalimide derivative obtained in the above Reference example 21 dissolved in 80 ml of acetone were added 4.64 g (0.0336 mole) of potassium carbonate and 1.39 ml (0.0224 mole) of methyl iodide under argon atmosphere, and the mixture was stirred vigorously at room temperature overnight. The reaction mixture was concentrated under reduced pressure, and the residue was extracted with ethyl acetate. The ethyl acetate layer was washed with water and then with a saturated saline solution, and dried over anhydrous sodium sulfate. The solvent was removed under reduced pressure, and the residue was recrystallized from a mixed solvent of ethyl acetate and hexane to obtain 3.22 g of the title compound as pale yellow crystals. Recrystallization again from the mother liquor was carried out again to obtain further 0.70 g of the title compound. Melting point: 207° to 208° C., IR (Nujol) (cm$^{-1}$): 1725, 1515, 1490, 1220, 1040, 835, 715, 655, 560, 520, 475, MS (DI, m/z): 416 (M+, base), 401 (M+-Me), 373, 343, 241, 226, 198

Reference Example 24

5-methoxy-1-(4-fluorophenyl)-3-ethyl-3-(benzyloxycarbonylamino)-2,3-dihydro-1H-indol-2-one A mixture of 2.00 g (0.00493 mole) of the benzyloxycarbonylamino derivative obtained in the above Reference example 22, 4.00 g of ethyl iodide, 2.50 g of potassium carbonate and 30 ml of dimethylformamide (DMF) was stirred under argon atmosphere at room temperature overnight. The reaction mixture was diluted with water and extracted with ethyl acetate, and the extract was washed with water and dried over anhydrous sodium sulfate. The solvent was removed under reduced pressure, and the residue was purified by silica gel column chromatography (eluent; chloro form: ethyl acetate (15:1 v/v)) to obtain 1.91 g of the title compound as a colorless oily product. FAB-MS (m/z): 435 (MH+)

Reference Example 25

5-methoxy-1-(4-fluorophenyl)-3-n-butyl-(benzyloxycarbonylamino)-2,3-dihydro-1H-indol-2-one A mixture of 2.03 g (0.005 mole) of the benzyloxycarbonylamino derivative obtained in the above Reference example 22, 3.00 g of n-butyl iodide, 2.50 g of potassium carbonate and 30 ml of DMF was reacted and purified in the same manner as in Reference example 24 to obtain 2.20 g of the title compound as a reddish brown oily product. FAB-MS (m/z): 463 (MH+)

Reference Example 26

5-methoxy-1-(4-fluorophenyl)-3-methyl-(benzyloxycarbonylamino)-2,3-dihydro-1H-indol-2-one A mixture of 21.7 g (0.0517 mole) of the benzyloxycarbonylamino derivative obtained in the above Reference example 22, 29 g of methyl iodide, 16.8 g of potassium carbonate and 80 ml of DMF was reacted and treated in the same manner as in Reference example 24, and recrystallized from a mixed solvent of ethyl acetate and hexane to obtain 20.7 g of the title compound as colorless needle crystals. Melting point: 155.5° to 156° C.

Reference Example 27

5-methoxy-1-(4-fluorophenyl)-3-isopropyl-(benzyloxycarbonylamino)-2,3-dihydro-1H-indol-2-one A mixture of 3.0 g (0.00739 mole) of the benzyloxycarbonylamino derivative obtained in the above Reference example 22, 3.77 g of isopropyl iodide, 3.05 g of potassium carbonate and 30 ml of DMF was reacted and purified in the same manner as in Reference example 24 to obtain 2.83 g of the title compound as an oily product. EI-MS (m/z): 448 (M+)

Reference Example 28

3-amino-3-methyl-1-(4-fluorophenyl)-5-methoxy-2,3-dihydro-1H-indol-2-one

To a solution of 3.20 g (0.00768 mole) of the 3-methyl-indol-2-one derivative obtained in the above Reference example 23 dissolved in a mixed solvent of 30 ml of tetrahydrofuran and 30 ml of ethanol was added dropwise 447 μl (0.00922 mole) of hydrazine hydrate at room temperature, and the mixture was stirred overnight. Thereafter, to the mixture were added 20 ml of tetrahydrofuran, 20 ml of ethanol and 447 μl of hydrazine hydrate, and the mixture was refluxed for 8 hours. After the reaction mixture was cooled to room temperature, insolubles precipitated were removed by filtration and the filtrate was concentrated to obtain a residue. The residue was dissolved again in ethyl acetate. Insolubles were removed by filtration, and the filtrate was concentrated under reduced pressure. The residue was purified by silica gel column chromatography (eluent; chloroform: ethyl acetate (1:1 v/v)) to obtain 2.10 g of the title compound as colorless needle crystals. Melting point: 163° to 164° C., IR (Nujol) (cm$^{-1}$): 1710, 1610, 1490, 1225, 1200, 1000, 835, 715, 655, 560, 520, 475, FAB-MS (m/z): 287 (MH+), 286 (M+), 270 (M+-NH$_2$ base), 258 (M+-CO)

Reference Example 29

3-amino-3-ethyl-1-(4-fluorophenyl)-5-methoxy-2,3-dihydro-1H-indol-2-one

A mixture of 1.89 g (0.00435 mole) of the benzyloxycarbonylamino derivative obtained in the above Reference example 24, 0.50 g of 10% Pd—C (50% wet by weight), 2.0 ml of 10% HCl and 30 ml of ethanol was subjected to catalytic reduction for 3 hours under hydrogen atmosphere of an atmospheric pressure (1 atm). The catalyst was removed by filtration, and the solvent was removed under reduced pressure. The residue was treated with sodium hydrogen carbonate and extracted with ethyl acetate. The ethyl acetate layer was washed with water and dried over anhydrous sodium sulfate, and the solvent was removed under reduced pressure. The residue was purified by silica gel column chromatography (eluent:chloroform:ethyl acetate (5:1 to 6:1 v/v) to obtain 1.14 g of the title compound as a colorless oily product. FAB-MS (m/z): 301 (MH+), 300 (M+)

Reference Example 30

3-amino-3-n-butyl-1-(4-fluorophenyl)-5-methoxy-2,3-dihydro-1H-indol-2-one

In the same manner as in Reference example 29, from the corresponding benzyloxycarbonylamino derivative obtained in Reference example 25, 1.20 g of the title compound was obtained as a pale brown oily product. FAB-MS (m/z): 329 (MH+), 328 (M+)

Reference Example 31

3-amino-3-methyl-1-(4-fluorophenyl)-5-methoxy-2,3-dihydro-1H-indol-2-one

In the same manner as in Reference example 29, from the corresponding benzyloxycarbonylamino derivative obtained in Reference example 26, the title compound was obtained as colorless needle crystals. Melting point: 162.5° to 163.5° C.

Reference Example 32

3-amino-3-isopropyl-1-(4-fluorophenyl)-5-methoxy-2,3-dihydro-1H-indol-2-one

In the same manner as in Reference example 29, from the corresponding benzyloxycarbonylamino derivative obtained in Reference example 27, the title compound was obtained as a pale yellow oily product. EI-MS (m/z) 314 (M+)

Reference Example 33

1,2-di(t-butoxycarbonyl)-1-(1-phenyl-3,4-dihydroquinolin-2 (1H)-on-3-yl)-hydrazine To a solution of 0.45 g (0.00448 mole) of diisopropylamine dissolved in 20 ml of tetrahydrofuran was added dropwise 2.6 ml (0.00448 mole) of n-butyl lithium (a 1.6M hexane solution) at 0° C., and the mixture was stirred for 20 minutes. After the mixture was cooled to −78° C., to the mixture was added dropwise a solution of 1.00 g (0.00448 mole) of 1-phenyl-3,4-dihydroquinolin-2 (1H)-one dissolved in 10 ml of tetrahydrofuran, and the mixture was stirred at the same temperature for 30 minutes. Next, to the mixture was added dropwise a solution of 2.06 g of di-t-butyl azodicarboxylate dissolved in 10 ml of tetrahydrofuran, and the mixture was stirred at −78° C. for one hour. After completion of the reaction, the reaction mixture was treated with an ammonium chloride aqueous solution, extracted with chloroform and dried over anhydrous sodium sulfate. Chloroform was removed under reduced pressure, and the residue was purified by silica gel column chromatography (eluent:ethyl acetate:hexane (1:5 v/v)) to obtain 1.41 g of the title compound as a colorless caramel-like product.

Reference Example 34

3-amino-1-phenyl-3,4-dihydroquinolin-2 (1H)-one

To a solution of 1.02 g of the hydrazine derivative obtained in the above Reference example 33 dissolved in 10 ml of dichloromethane was added 10 ml of trifluoroacetic acid, and the mixture was stirred at room temperature for 30 minutes. After completion of the reaction, the solvent was removed under reduced pressure, and the residue was extracted with ethyl acetate. The ethyl acetate layer was washed with a 10% sodium hydroxide aqueous solution and then with water, and dried over anhydrous sodium sulfate. Ethyl acetate was removed under reduced pressure, and the oily residue was dissolved in 10 ml of methanol. To the solution was added 0.4 g of a platinum oxide catalyst, and the mixture was subjected to catalytic reduction at normal temperature for 4 hours under hydrogen atmosphere. The catalyst was removed by filtration, and the filtrate was concentrated under reduced pressure. To the residue was added 10% hydrochloric acid, and the mixture was washed with ethyl acetate. The aqueous layer was made alkaline by adding a 10% sodium hydroxide aqueous solution, extracted with ethyl acetate and dried over anhydrous sodium sulfate. Ethyl acetate was removed under reduced pressure, and the residue was recrystallized from ethyl acetate to obtain 0.443 g of the title compound. Melting point: 108° to 110° C., NMR (CDCl$_3$) (δ): 1.4 to 2.3 (2H, br.s, NH$_2$), 2.9 to 3.4 (2H, m), 3.3 to 4.05 (1H, br), 6.3 to 6.4 (1H, m), 6.9 to 7.7 (8H, m)

Reference Example 35

3-azido-1-phenyl-2,3, 4,5-tetrahydro-1-benzoazepin-2(1H)-one

A suspension of 5.0 g (0.0184 mole) of 3-chloro-1-phenyl-2,3,4,5-tetrahydro-1-benzoazepin-2(1H)-one and 1.8 g (0.0277 mole) of sodium azide suspended in 50 ml of dimethylformamide was stirred at a bath temperature of 80° C. overnight. Next, to the mixture was added 1.0 g (0.0154 mole) of sodium azide, and the mixture was stirred for 8 hours. The reaction mixture was diluted with water and then extracted with ethyl acetate. The ethyl acetate layer was washed with water and dried, and the solvent was removed under reduced pressure to obtain a residue. The residue was recrystallized from ethyl acetate to obtain 3.58 g of the title compound as colorless crystals.

Melting point: 141° to 143° C.

Reference Example 36

3-amino-1-phenyl-2,3,4,5-tetrahydro-1-benzoazepin-2(1H)-one

A mixture of 3.30 g (0.0119 mole) of the azide derivative obtained in the above Reference example 35, 3.0 g (0.0476 mole) of ammonium formate, 0.35 g of 5% palladium-carbon and 150 ml of methanol was refluxed for 2 hours. The catalyst was removed by filtration, the filtrate was concentrated under reduced pressure, and the residue was extracted with ethyl acetate. The ethyl acetate layer was washed with a saturated sodium hydrogen carbonate aqueous solution and then with water, and dried over anhydrous sodium sulfate. The solvent was removed under reduced pressure, and the residue was recrystallized from a mixed solvent of ethyl acetate and hexane to obtain 2.03 g of the title compound as colorless crystals. Melting point: 109.5° to 110.5° C., IR (Nujol) (cm$^{-1}$): 3370, 3310, 1670, MS (DI, m/z): 252 (M$^+$)

Reference Example 37 optical resolution of 3-amino-3-methyl-1-(4-fluorophenyl)-5-methoxy-2,3-dihydro-1H-indol-2-one A mixture of 9.26 g of dl-3-amino-3-methyl-1-(4-fluorophenyl)-5-methoxy-2,3-dihydro-1H-indol-2-one and 11.72 g of dibenzoyl-L-tartaric acid (hereinafter referred to as "DBT") was dissolved in 80 ml of hot ethyl acetate. After removal of solvent, the residue was recrystallized from 40 ml of ethyl acetate and 20 ml of diisopropyl ether to afford 7.71 g of a (-)-DBT salt of the corresponding (S)-isomer as colorless powder.

Melting point: 164.5° to 167° C. (decomposed), $[\alpha]_D^{20}$: −78.12° (c=0.896, MeOH)

Optical purity: 99.7% ee (measured by optically active HPLC described below)

Free base: (S)-3-amino-3-methyl-1-(4-fluorophenyl)-5-methoxy-2,3-dihydro-1H-indol-2-one Melting point: 160° to 161° C. $[\alpha]_D^{25}$: −72.38° (c=1.014, CHCl$_3$)

The mother liquor was concentrated, and the residue was extracted with ethyl acetate. The extract was treated with a sodium hydrogen carbonate aqueous solution, washed with water and then a saline solution, and dried over anhydrous sodium sulfate, and the solvent was removed under reduced pressure. To the residue was added 6.45 g of dibenzoyl-D-tartaric acid, and the mixture was dissolved in 20 ml of ethyl acetate by heating. After cooling, crystals precipitated were collected by filtration, washed with 30 ml of diisopropyl ether and ethyl acetate (1:1 v/v) and dried to obtain 8.31 g of a (+) DBT salt of the corresponding (R)-isomer as colorless powder.

Melting point: 163.0° to 164° C. (decomposed) $[\alpha]_D^{25}$: +76.29° (c=0.928, MeOH)

Optical purity: 99.9% ee (measured by optically active HPLC described below)

Free base: (R)-3-amino-3-methyl-1-(4-fluorophenyl)-5-methoxy-2,3-dihydro-1H-indol-2-one Melting point: 160° to 161° C. $[\alpha]_D^{25}$: +74.05° (c=1.426, CHCl$_3$)

Determination of an absolute configuration was carried out by X-ray analysis of a 3-(p-toluenesulfonylamino) derivative of the above compound.

Measurement of optical purity

Conditions of HPLC

Column: Opti Pac XC 3.9×300 mm (trade name, produced by Waters Co.)

Eluent: hexane:isopropanol (50:50 v/v)

Flow rate: 0.5 ml/min

Detection wavelength: UV 254 nm

Under the above conditions, the dl isomers could be separated.

Retention time (R)-isomer: 9.27 min (S)-isomer: 15.80 min

Reference Example 38 optical resolution of 3-amino-3-methyl-1-(2-fluorophenyl)-2,3-dihydro-1H-indol-2-one In the same manner as in Reference example 37, the following compounds were obtained from the corresponding starting materials, respectively.

(−) DBT salt of (R)-isomer:

Melting point: 167.5° to 169.5° C. $[\alpha]_D^{20}$: −60.14° (c=0.562, MeOH) 99.3% ee Free base: (R)-3-amino-3-methyl-1-(2-fluorophenyl)-2,3-dihydro-1H-indol-2-one $[\alpha]_D$: +63.33° (c=0.960, CHCl$_3$)

(+) DBT salt of (S)-isomer:

Melting point: 165.5° to 167° C. $[\alpha]_D^{20}$: +59.51° (c=0.578, MeOH) 99.2% ee Free base: (S)-3-amino-3-methyl-1-(2-fluorophenyl)-2,3-dihydro-1H-indol-2-one $[\alpha]_D^{20}$: −63.40° (c=0.936, CHCl$_3$)

Reference Example 39 optical resolution of 3-amino-3-methyl-1-phenyl-5-methoxy-2,3-dihydro-1H-indol-2-one In the same manner as in Reference example 37, the following compounds were obtained from corresponding starting materials, respectively.

(+) DBT salt of (−)-isomer:

Melting point: 166° to 167° C. $[\alpha]_D^{20}$: +61.57° (c=0.419, MeOH) 99.2% ee Free base: (−)-3-amino-3-methyl-1-phenyl-5-methoxy-2,3-dihydro-1H-indol-2-one $[\alpha]_D^{20}$: −72.15° (c=0.553, CHCl$_3$)

(−) DBT salt of (+)-isomer:

Melting point: 158° to 160° C. $[\alpha]_D^{20}$: −61.92° (c=0.436, MeOH) 99.5% ee Free base: (+)-3-amino-3-methyl-1-phenyl-5-methoxy-2,3-dihydro-1H-indol-2-one [α]$_D^{20}$: +73.68° (c=0. 418, CHCl$_3$)

Reference Example 40

3-Benzyloxycarbonylamino-1-(3-chlorophenyl)-6-methoxy-2,3-dihydro-1H-indol-2-one In the same manner as in Reference example 22, the title compound was obtained from 3-amino-1-(3-chlorophenyl)-6-methoxy-2,3-dihydro-1H-indol-2-one hydrochloride as pale yellow needles.

Melting point: 158.5° to 160° C., MS (m/z): 422 (M+)

Reference Example 41

3-Benzyloxycarbonylamino-1-(4-fluorophenyl)-6-methoxy-2,3-dihydro-1H-indol-2-one In the same manner as in Reference example 22, the title compound was obtained from 3-amino-1-(4-fluorophenyl)-6-methoxy-2,3-dihydro-1H-indol-2-one hydrochloride as colorless needles.

Melting point: 184° to 185° C., MS (m/z): 406 (M+)

Reference Example 42

3-Benzyloxycarbonylamino-1-(2-fluorophenyl)-6-methoxy-2,3-dihydro-1H-indol-2-one In the same manner as in Reference example 22, the title compound was obtained from 3-amino-1-(2-fluorophenyl)-6-methoxy-2,3-dihydro-1H-indol-2-one hydrochloride.

Melting point: 178° to 182° C., MS (m/z): 406 (M+)

Reference Example 43

3-Benzyloxycarbonylamino-3-methyl-1-(3-chlorophenyl)-6-methoxy-2,3-dihydro-1H-indol-2-one In the same manner as in Reference example 23, from the corresponding benzyloxycarbonylamino derivative obtained in Reference example 40, the title compound was obtained as pale brown solid.

Melting point: 143° to 144° C., MS (m/z): 436 (M+)

Reference Example 44

3-Benzyloxycarbonylamino-3-methyl-1-(4-fluorophenyl)-6-methoxy-2,3-dihydro-1H-indol-2-one In the same manner as in Reference example 23, from the corresponding benzyloxycarbonylamino derivative obtained in Reference example 41, the title compound was obtained as colorless needles.

Melting point: 167° to 169° C., MS (m/z): 420 (M+)

Reference Example 45

3-Benzyloxycarbonylamino-3-methyl-1-(2-fluorophenyl)-6-methoxy-2,3-dihydro-1H-indol-2-one In the same manner as in Reference example 23, from the corresponding benzyloxycarbonylamino derivative obtained in Reference example 42, the title compound was obtained as pale yellow needles.

Melting point: 149° to 151° C., MS (m/z): 420 (M+)

Reference Example 46

3-Amino-3-methyl-1-(3-chlorophenyl)-6-methoxy-2,3-dihydro-1H-indol-2-one

In the same manner as in Reference example 29, from the corresponding benzyloxycarbonylamino derivative obtained in Reference example 43, the title compound was obtained as colorless needles.

Melting point: 234° to 235° C. (decomposed), MS (m/z): 302 (M+)

Reference Example 47

3-Amino-3-methyl-1-(4-fluorophenyl)-6-methoxy-2,3-dihydro-1H-indol-2-one

In the same manner as in Reference example 29, from the corresponding benzyloxycarbonylamino derivative obtained in Reference example 44, the title compound was obtained as colorless needles.

Melting point: 140° to 141° C., MS (m/z): 286 (M+)

Reference Example 48

3-Amino-3-methyl-1-(2-fluorophenyl)-6-methoxy-2,3-dihydro-1H-indol-2-one

In the same manner as in Reference example 29, from the corresponding benzyloxycarbonylamino derivative obtained in Reference example 45, the title compound was obtained as oily product.

MS (m/z): 286 (M+)

The compounds of the present invention or a salt thereof have an excellent antagonistic action on cholecystokinin receptor and exhibits an excellent activity in inhibiting the secretion of pancreatic juice so that they are useful as a prophylactic or curing agent for diseases of the digestive system such as pancreatic disorders and gastrointestinal diseases. For example, 3-{9H-pyrido[3,4-b]-indol-3-yl-carbonyl}-amino-3-methyl-1-phenyl-2-indolinone (10 mg/kg i.v.) significantly inhibited the pancreatic secretion induced by CCK-8 in rats. Further, the compound of the present invention have a low toxicity so that they can be a medicine having high safety.

We claim:

1. A β-carboline compound represented by the formula:

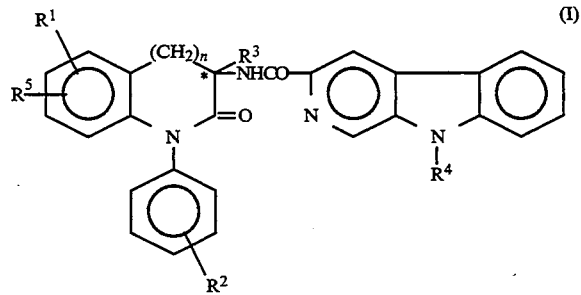

wherein R$^1$ represents hydrogen atom, a lower alkyl group, a lower alkoxy group or hydroxy group; R$^5$ represents hydrogen atom, or R$^1$ and R$^5$ are bonded to represent a lower alkylenedioxy group; R$^2$ represents hydrogen atom, a halogen atom, a lower alkoxy group or hydroxy group; R$^3$ represents hydrogen atom, a carbamoyl lower alkyl group, a lower alkyl group, a carboxy lower alkyl group or a lower alkoxycarbonyl lower alkyl group; R$^4$ represents hydrogen atom, a lower alkyl group, a carboxy lower alkyl group, a lower alkoxycarbonyl lower alkyl group, a lower alkanoyl group, an arylcarbonyl group, a lower alkanesulfonyl group, a lower alkoxycarbonyl group, an aralkyl group, formyl group or a di(lower alkyl)sulfamoyl group; n represents 0, 1 or 2; and the symbol * represents an asymmetric carbon atom, or a pharmaceutically acceptable salt thereof.

2. The compound according to claim 1, wherein the compound of the formula (I) is an optical isomer based on the asymmetric carbon atom *.

3. The compound according to claim 1, wherein $R^1$ is hydrogen atom, a lower alkyl group, a lower alkoxy group or hydroxy group, $R^2$ is hydrogen atom or a halogen atom, $R^3$ is hydrogen atom, a lower alkyl group, a carboxy lower alkyl group or a lower alkoxycarbonyl lower alkyl group, $R^4$ is hydrogen atom, a lower alkyl group or a lower alkanoyl group, and $R^5$ is hydrogen atom.

4. The compound according to claim 3, wherein $R^1$ is hydrogen atom or a lower alkoxy group, $R^2$ is hydrogen atom or a halogen atom, $R^3$ is hydrogen atom, a lower alkyl group or a lower alkoxycarbonyl lower alkyl group, $R^4$ is hydrogen atom or a lower alkanoyl group, and $R^5$ is hydrogen atom.

5. The compound according to claim 4, wherein $R^1$ is hydrogen atom or methoxy group, $R^2$ is hydrogen atom or fluorine atom, $R^3$ is hydrogen atom, methyl group or methoxycarbonylethyl group, $R^4$ is hydrogen atom or acetyl group, and $R^5$ is hydrogen atom.

6. The compound according to claim 5, wherein $R^1$ is methoxy group, $R^2$ is fluorine atom, $R^3$ is methyl group, $R^4$ is acetyl group, and $R^5$ is hydrogen atom.

7. The compound according to claim 6, wherein n is 0.

8. A pharmaceutical composition which comprises a therapeutically effective amount of the compound as set forth in claim i in admixture with a conventional pharmaceutically acceptable carrier or diluent.

9. A pharmaceutical composition which comprises a therapeutically effective amount of the compound as set forth in claim 2 in admixture with a conventional pharmaceutically acceptable carrier or diluent.

10. A pharmaceutical composition which comprises a therapeutically effective amount of the compound as set forth in claim 3 in admixture with a conventional pharmaceutically acceptable carrier or diluent.

11. A pharmaceutical composition which comprises a therapeutically effective amount of the compound as set forth in claim 4 in admixture with a conventional pharmaceutically acceptable carrier or diluent.

12. A pharmaceutical composition which comprises a therapeutically effective amount of the compound as set forth in claim 5 in admixture with a conventional pharmaceutically acceptable carrier or diluent.

13. A pharmaceutical composition which comprises a therapeutically effective amount of the compound as set forth in claim 6 in admixture with a conventional pharmaceutically acceptable carrier or diluent.

14. A pharmaceutical composition which comprises a therapeutically effective amount of the compound as set forth in claim 7 in admixture with a conventional pharmaceutically acceptable carrier or diluent.

* * * * *